United States Patent
Delisle

(10) Patent No.: US 9,808,639 B2
(45) Date of Patent: Nov. 7, 2017

(54) INTUITIVE OVERLAID READINESS INDICATOR FOR DEFIBRILLATORS

(71) Applicant: KONINKLIJKE PHILIPS N.V., Eindhoven (NL)

(72) Inventor: Norman Maurice Delisle, Manchester, MA (US)

(73) Assignee: Koninklijke Philips N.V., Eindhoven (NL)

( * ) Notice: Subject to any disclaimer, the term of this patent is extended or adjusted under 35 U.S.C. 154(b) by 7 days.

(21) Appl. No.: 14/655,974

(22) PCT Filed: Dec. 17, 2013

(86) PCT No.: PCT/IB2013/061010
§ 371 (c)(1),
(2) Date: Jun. 26, 2015

(87) PCT Pub. No.: WO2014/102658
PCT Pub. Date: Jul. 3, 2014

(65) Prior Publication Data
US 2015/0335902 A1  Nov. 26, 2015

Related U.S. Application Data

(60) Provisional application No. 61/745,830, filed on Dec. 26, 2012.

(51) Int. Cl.
| | |
|---|---|
| *G06F 11/32* | (2006.01) |
| *A61N 1/39* | (2006.01) |
| *G06F 19/00* | (2011.01) |
| *G06F 11/30* | (2006.01) |

(52) U.S. Cl.
CPC ........ *A61N 1/3968* (2013.01); *A61N 1/3993* (2013.01); *G06F 11/321* (2013.01); *G06F 19/3412* (2013.01); *A61N 1/3925* (2013.01); *G06F 11/30* (2013.01); *G06F 11/32* (2013.01); *G06F 11/324* (2013.01)

(58) Field of Classification Search
CPC ... A61N 1/3993; A61N 1/3925; G06F 11/324; G06F 11/30; G06F 11/32; G06F 11/321
See application file for complete search history.

(56) References Cited

U.S. PATENT DOCUMENTS

| | | | |
|---|---|---|---|
| 5,797,969 A | 8/1998 | Olson et al. | |
| 5,800,460 A * | 9/1998 | Powers | 607/5 |
| 2004/0164166 A1 | 8/2004 | Mahany et al. | |
| 2008/0177341 A1 | 7/2008 | Bowers | |
| 2015/0335902 A1 | 11/2015 | Delisle | |

FOREIGN PATENT DOCUMENTS

| | | | |
|---|---|---|---|
| WO | 0051520 A2 | 9/2000 | |
| WO | WO 0051520 A2 * | 9/2000 | G01N 33/558 |
| WO | 2011066574 A1 | 6/2011 | |

* cited by examiner

Primary Examiner — Benyam Haile

(57) ABSTRACT

A fail-safe visual indicator (62) for indicating the readiness status of a medical device is described. The visual indicator incorporates iconic status indications (67, 70) which are easier to understand for users of all nationalities and languages. The status indications are superimposed upon each other in order to reduce the space required on the medical device for the indicator.

19 Claims, 6 Drawing Sheets

10

16

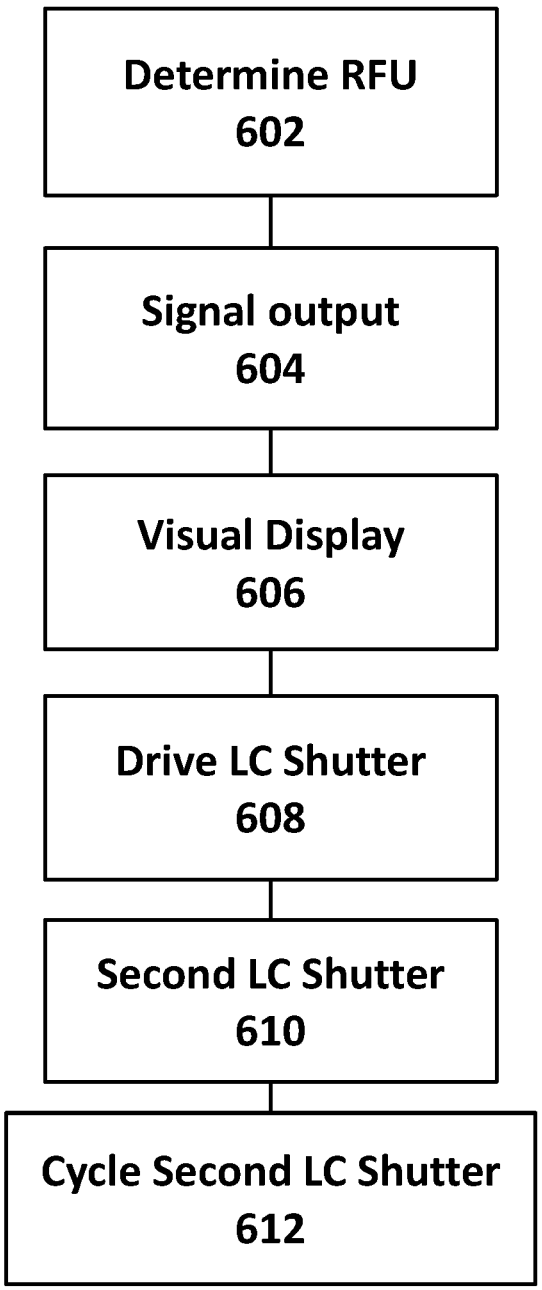

INTUITIVE OVERLAID READINESS INDICATOR FOR DEFIBRILLATORS

This application is a national stage application under 35 U.S.C. §371 of International Application No. PCT/1132013/061010 filed on Dec. 17, 2013 and published in the English language on Jul. 3, 2014 as International Publication No. WO 2014/102658 A1, which claims priority to U.S. Application No. 61/745,830 filed on Dec. 26, 2012, the entire disclosures of which are incorporated herein by reference.

The invention relates to an improved apparatus and method for automatic self-testing of a medical device, and in particular to an improved visual indicator for displaying the readiness status of the device when the device is operating, when it is standing-by (i.e. off with power) and when it is without power. The method and apparatus is particularly useful for a device such as a crash-cart hospital defibrillator-monitor, a frequently-used defibrillator employed by Emergency Medical Services (EMS) teams, and for an automatic external defibrillator (AED) that normally operates in a standby mode for long periods of time between uses.

Electro-chemical activity within a human heart normally causes the heart muscle fibers to contract and relax in a synchronized manner that results in the effective pumping of blood from the ventricles to the body's vital organs. Sudden cardiac death is often caused by ventricular fibrillation (VF) in which abnormal electrical activity within the heart causes the individual muscle fibers to contract in an unsynchronized and chaotic way. The only effective treatment for VF is electrical defibrillation in which an electrical shock is applied to the heart to allow the heart's electro-chemical system to re-synchronize itself. Once organized electrical activity is restored, synchronized muscle contractions usually follow, leading to the restoration of cardiac rhythm. But it is critical to defibrillate VF within just a few minutes after its onset for the treatment to be effective.

The necessity to apply defibrillation quickly after onset of VF has given rise to external defibrillators such as crash-cart advanced life support defibrillators, EMS defibrillator-monitors, and automatic external defibrillators (AEDs) which may be used by first responders and lay people. AEDs especially may remain unused for long periods of time and yet must be ready to operate reliably in an emergency situation. To ensure operational readiness, many defibrillators employ a self-test operation that is conducted at regular intervals. The MRx defibrillator, the XL+ defibrillator, and the Heartstream Forerunner AED, all manufactured by Philips Medical Systems of Andover Mass., for example, each employ a self-test system that generates self-test operations automatically in response to a predetermined schedule. The self-test operation typically includes a number of different system checks including functional, calibration, and safety tests to verify that the defibrillator's components and operation are within predetermined specifications. The high voltage (HV) circuit is a critical component of the defibrillator that provides the defibrillation pulse. Verification of the proper functioning of the defibrillator is a typical part of any self-test operation.

Device readiness indicators are commonly used in medical devices to inform the user whether or not the device is ready-for-use (RFU). A medical device such as a defibrillator is used in an emergency situation where every second counts. But because a defibrillator is turned-off most of the time, standard clinical practices call for the staff to periodically determine whether the device is ready for use if needed. These devices typically perform automatic self-tests on an hourly or daily basis when they are turned off. The readiness indicator provides a highly-visible readiness indication. The readiness indicator operates continuously when the device is turned on, turned off, and even when there is no power applied to the device (e.g. neither AC power nor battery power available). If the defibrillator is being used in a hospital or EMS environment, staff is typically tasked with checking the readiness indication during shift checks.

The R-Series defibrillators manufactured by Zoll Corporation of Chelmsford Mass., for example, include a visual indicator 10 having a "not-ready" graphic 12 arranged alongside an illuminated "ready-for-use" graphic 14. LCD shutters are arranged over each graphic. One or the other LCD shutter is driven opaque depending on the sensed readiness, to indicate the readiness status to the user. FIG. 1a illustrates this particular indicator.

Each of the MRx, the XL+, and the Heartstream Forerunner AED include a visual indicator 16 for showing the result of the most recent self-test operation, and thus its readiness state while in standby. Each of these defibrillators also includes a liquid crystal display (LCD) shutter that is driven shut (opaque) by the self-test system when the most-recent self-test has been successful, as shown by element 19 of FIG. 1b. The opaque shutter obscures an underlying "red-X" graphic 18 to indicate to the user that the AED is ready for use. The opaque portion of the LCD shutter is shaped like an hourglass to block the "X" elements of the graphic. When the LCD shutter is de-energized because of either power failure or a "not-ready" determination, the shutter is transparent so that the "red X" graphic 18 is displayed.

U.S. Pat. No. 5,800,460, "Method for Performing Self-Test in a Defibrillator", issued Sep. 1, 1998 to Powers et al. and incorporated herein by reference, describes a status indicator for a defibrillator which includes a fail-safe visual display having a multiple-part LCD. A top plate of the LCD is a clear window with an "OK" symbol printed on its back. A middle plate is an LCD shutter that is biased so as to be opaque when driven by the system monitor via a drive signal. A bottom plate has an international "Not" symbol on its top surface. The middle plate also includes a separately addressable portion driven by the system monitor via AC-coupled drive. In operation, the system monitor drives the LCD shutter only when confirmation of successful testing is received within an expected time window, such that only the top plate "OK" is shown against the opaque shutter. The shutter is transparent when de-energized as a result of unsuccessful testing or power failure, such that the "OK" appears superimposed over the "Not" symbol to indicate a "Not OK" to the user.

Each of the afore-described references is directed to indicating the readiness status of a defibrillator before it is used in a cardiac arrest rescue. But each prior readiness indicator is suboptimal, lacking one or more of the following important properties. First, the ready-for-use and not-ready-for-use states must be easily recognizable to all users across all nationalities. Although the "X" shape is easily recognized by all users as a failure indication, the hourglass shape and "OK" symbol are not easily recognized as a "ready-for-use" indication across all countries and cultures in which the device is used. Second, the indicator must be fail-safe, wherein the "not ready" state must be displayed even when no power is available to the device indicator. An illuminated readiness indicator, such as that using a light emitting diode (LED), does not meet this criterion because the indicator requires power to be seen. Third, the readiness indicator must be large enough to be seen from a room-length distance, but must not occupy too much space on the front panel of the medical device. A side-by-side visual indicator as described above requires twice as much space on the front panel as an overlaid indicator, reducing the space available for other rescue-related features. Also, the readiness indicator should provide an active indication that the medical device is ready for use, such as by a flashing symbol when appropriate. Therefore, what is needed is a readiness indicator which includes all of these properties.

In accordance with the principles of the present invention, an improved visual indicator for indicating the readiness status of a medical device such as a defibrillator is described. The visual indicator includes a liquid crystal (LC) shutter which overlays a graphic icon that indicates a not-ready-for use status. The LC shutter includes a transparent icon that indicates a ready-for-use status. When the medical device determines a ready-for-use status, it drives the LC shutter to an opaque state such that the transparent icon is visible and a substantial portion of the graphic icon is obscured.

Also in accordance with the principles of the present invention is a medical device such as a defibrillator which automatically and periodically conducts self-tests to determine its readiness status. The readiness status is displayed on a visual indicator, similar to that described above, controlled by the device. The visual indicator is fail-safe such that a complete loss of power causes the indicator to show a not-ready-for-use status.

Also in accordance with the principles of the present invention is a method for displaying the readiness status of a medical device. The method steps include driving a visual indicator using a control signal from a self-test circuit in order to make visible a transparent icon disposed on an LC shutter. The transparent icon indicates that the device is ready-for-use. The method may also include a step of cyclically flashing the transparent icon on and off.

IN THE DRAWINGS

FIG. 6 is a flow chart illustrating the method for displaying the operating status of a defibrillator according to one embodiment of the present invention.

Figure 1A:
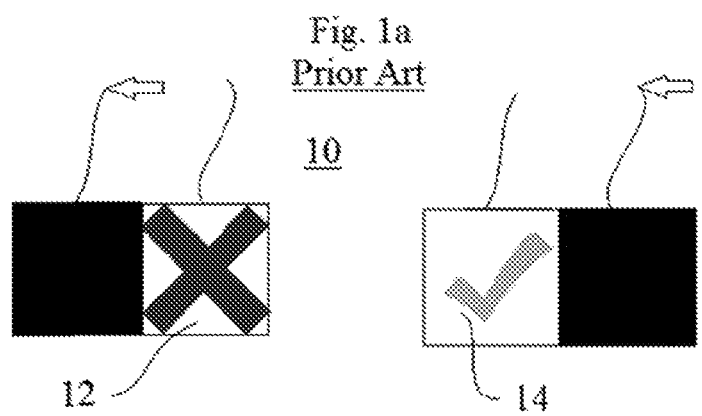
FIG. 1a illustrates one prior art visual indicator for showing a defibrillator readiness status.
Figure 1B:
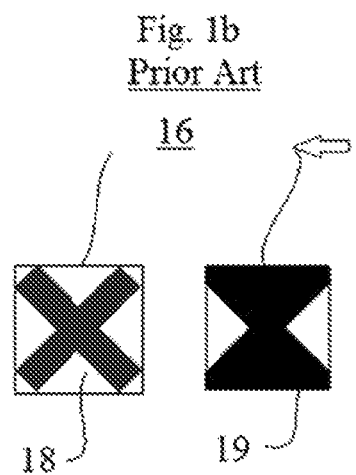
FIG. 1b illustrates another such prior art visual indicator.
Figure 2:
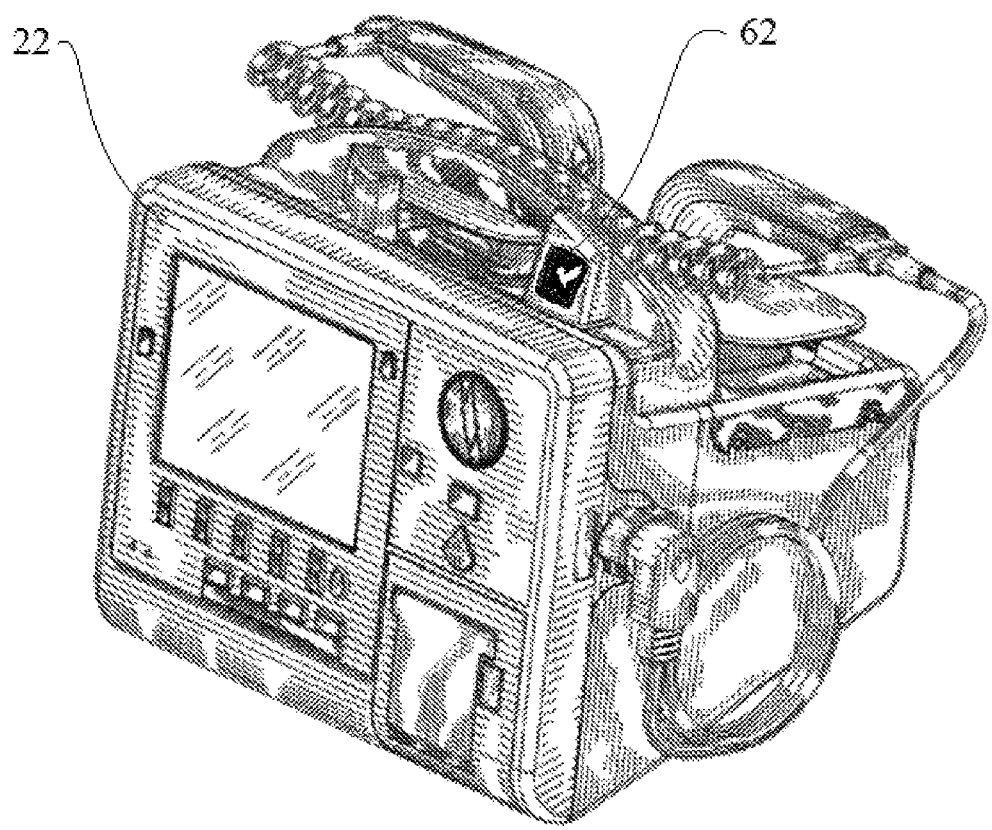
FIG. 2 illustrates a defibrillator having a visual indicator according to one embodiment of the present invention.

Now turning to the illustrations, FIG. 2 illustrates one embodiment of the invention having a readiness indicator 62, elsewhere referred to as a visual indicator display 62, disposed on the exterior housing of a medical device. Here, the exemplary medical device is a defibrillator 22. Other medical devices having internal self-testing features, such as patient monitors or ultrasound machines, may also employ the inventive readiness indicator.

As shown in FIG. 2, readiness indicator 62 is easily viewable at a distance from the medical device. In this embodiment, the ready-for-use indication on indicator 62 is a check mark, which is a universally recognized indication that the device is operable.

Figure 3:
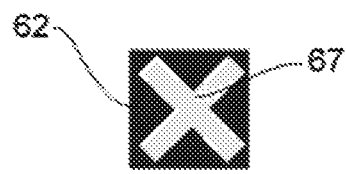
FIG. 3 illustrates the visual indicator of the present invention in the driven and un-driven states.
Figure 3:
Figure 3:

FIG. 3 illustrates a more detailed view of the readiness indicator 62 according to a preferred embodiment of the invention. This embodiment combines the universally-recognized graphic iconic symbols of an "X" 67 and a check-mark 71 in an overlaid construction. The graphic X icon 67 is screen printed or displayed as a background image. Overlaying the graphic X icon 67 is an electronic shutter such as a monochromatic liquid crystal (LC) shutter 64. When no power is applied to the LC shutter 64, the LC is transparent and therefore the graphic X icon 67 shows, as seen in the upper left image of FIG. 3.

The LC shutter 64 further includes a transparent icon 70 which overlays a portion of the graphic X icon 67, as shown in the middle image of FIG. 3. Transparent icon 70 is arranged as a check mark. When power is applied to the LC shutter 64, its portions surrounding the transparent icon 70 check mark are driven opaque. The user thus sees the portions of the graphic X icon 67 through the transparent icon 70 in the shape of a check mark, as seen in the lower right illustration of FIG. 3.

Shading and coloration of the graphic X icon 67 enhances the visibility of the readiness indicator 62 further. The inventors have discovered that a white-appearing ready-for-use graphic on the dark (opaque) LC shutter 64 has the desired visibility for the user. However, it was not possible to display such a white-appearing transparent icon 70 on the prior art red-X graphic. Otherwise, the transparent icon 70 would appear to be red, a color which is universally recognized as a hazard color. Thus, such an icon appearance may convey conflicting meanings as to whether the device is really ready-to-use.

To overcome this problem, the colors of the graphic icon are shaded as a light, preferably white, "X" portion surrounded by a darker colored, preferably red, background. Thus, the not-ready-for-use indication shows red (i.e. hazard), whereas the ready-for-use indication shows only the non-alarming lighter shade over which the transparent portion lies.

Figure 4:
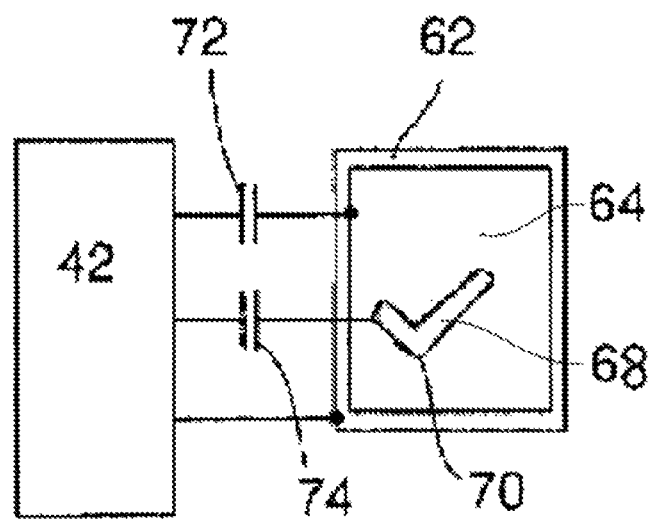
FIG. 4 is a functional block diagram of the automatic readiness status circuit of the visual indicator according to one embodiment of the present invention.

Now turning to FIG. 4, the control and driving circuit for the visual display 62 according to one embodiment of the invention is described. In a preferred embodiment, a defibrillator includes a readiness status circuit 42, which powers a status indicator to indicate the operational status of the defibrillator to a user. Readiness status circuit 42 operates in a standby mode to periodically check the hardware components and software components in the device. It also operates continuously when the device is operating. The readiness status circuit 42 takes inputs from both self-testing and run-time test components, not shown in FIG. 4, to check the operation of the device. If a failure is detected during clinical operations, the readiness status circuit 42 will cause the status indicator to indicate that failure immediately—it does not wait until the next self-test cycle.

The status indicator comprises a visual indicator display 62 comprising a graphic icon and at least one LC shutter 64. The status indicator optionally includes an audible output, such as a piezo buzzer, which beeps, chirps, or issues audible voice alerts when the defibrillator is not ready-for-use.

As previously described, visual display 62 comprises a graphic icon, such as the graphic X icon 67 shown in FIG. 3, which is selectively obscured by LC shutter 64 turning opaque when driven by the readiness status circuit 42 via control input 72. The LC shutter 64 also comprises a portion that is not coupled to drive 72, and which remains transparent. This portion is a transparent icon 70 which has the shape of a check mark or other universally recognizable symbol that the device is ready-for-use.

In operation, the readiness status circuit 42 drives LC shutter 64 only when it has confirmed a successful self-test. The visual display 62 would then appear as in FIG. 5(d). Failure to receive proper test confirmation causes the readiness status circuit 42 to cease issuing drive signals to LC shutter 64 via control input 72. LC shutter 64 will then go transparent, thereby exposing the underlying graphic icon 66 to view. The visual display 62 would then appear as in FIG. 5c. The readiness status circuit 42 may also then begin powering a piezoelectric failure alert buzzer at that time, preferably for 200 milliseconds, every 10 seconds, so long as there is power enough to do so.

The primary advantages of the visual display 62 of the preferred embodiment are its low power requirements and the fact that it must be powered to display a ready-for-use indication. The low power requirement is especially important in medical devices that are battery-powered, such as an AED. The latter advantage ensures the display's fail-safe nature, since the LC shutter 64 cannot be maintained opaque otherwise. Also, the transparent icon 70 may be devised as large as necessary for easy viewing, while enjoying a reduced footprint enabled by the overlay design.

Visual display 62 may also be enabled to separately drive transparent icon 70 into an opaque state. The readiness status circuit 42 periodically drives a second LC shutter 68, which is arranged coaxially with both the transparent icon 70 and the graphic icon, via a second LC shutter control input 74. Separately addressable transparent icon 70 then also serves as a positive indication (in addition to the fail-safe "checkmark" symbol) that the defibrillator has power and is functioning properly. Transparent icon 70 thus appears to flash or blink on and off periodically by means of the alternating driving and releasing of the drive control input 74 signal to second LC shutter 68.

Figure 5A:
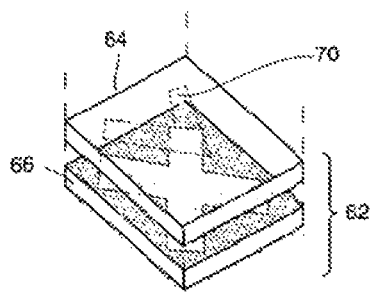
FIGS. 5a through 5d illustrate the physical disposition and the displayed appearance of the visual indicator according to one embodiment of the present invention.

Shown in FIG. 5a is one embodiment of the construction of readiness indicator 62. Graphic icon 66 is printed or formed on a base surface. The base surface may be reflective or may be back-lighted. One contemplated base surface is reflective and overlaid with a translucent colored plate. A background color is created from incident light passing through the colored plate, which is then reflected back out toward the user.

Overlying graphic icon 66 is LC shutter 64 having two portions. A driven portion becomes opaque in the presence of control input 72. The drivable portion of LC shutter 64 surrounds a transparent portion comprising a transparent icon 70. A thin layer of glass may overlay the LC shutter 64 for protection.

Figure 5B:
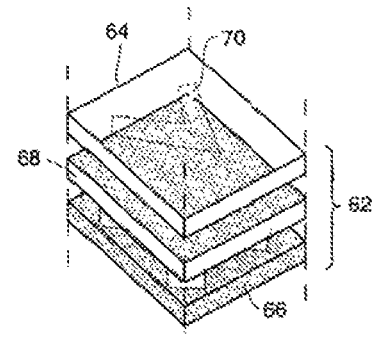

FIG. 5b illustrates an additional embodiment of readiness indicator 62, comprising three coaxial elements. The base layer with graphic icon 66 underlies the LC shutter 64 with transparent icon 70. A second LC shutter 68 is disposed in the stack, the operation of which obscures transparent icon 70 from the background color of graphic icon 66. Although the second LC shutter 68 is shown underlying LC shutter 64, it is understood that the scope of the invention includes a second LC shutter 68 overlying LC shutter 64, or a second LC shutter 68 that is co-extensive with and co-planar with transparent icon 70.

Figures 5C, 5D:
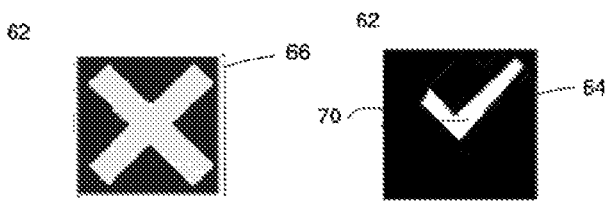

FIG. 5c illustrates the resulting appearance of readiness indicator 62 in the un-driven, not-ready-for-use, state. There, all LC shutters are transparent, and the underlying graphic icon 67 is visible to the user to convey that the device is not operable.

FIG. 5d illustrates the resulting appearance of visual readiness indicator 62 in the driven, ready-for-use, state. There, LC shutter 64 is driven opaque, leaving transparent icon 70 viewable as backlit by the light-colored portions of the underlying graphic icon 67. The appearance conveys to the user that the device is operable. If the second LC shutter 68 is employed, the transparent icon 70 may appear to flash on and off to convey a further operable status.

FIG. 6 illustrates a method for displaying the operating status of a medical device 600 such as a defibrillator 22, the method employing the visual readiness indicator 62 that has been previously described. The method 600 comprises the following steps. First, the defibrillator 22 automatically determines in step 602 by automatic self-testing whether it is ready-for-use. The automatic self-testing can be conducted during either standby or while the device is operating. If the defibrillator is ready-for-use, the defibrillator provides a positive control signal in step 604 from the defibrillator self-test circuit or a related control circuit. In step 606, a visual display is provided that is viewable to a user, and is thus preferably disposed on an external surface of the defibrillator. The visual display is similar to that previously described, and includes the graphic icon which indicates a not-ready-for-use status, a LC shutter overlaying the graphic icon. The LC shutter includes a transparent visual icon which indicates that the defibrillator is ready for use.

The positive control signal from the control circuit drives the LC shutter into an opaque state in step 608. When driven into the opaque state, all but the portion of the graphic icon which underlies the transparent visual icon is obscured by the LC shutter. The resulting display appears as a dark background on which is the transparent icon that indicates to the user a ready-to-use status. The color of the transparent icon is the un-obscured portion of the underlying graphic icon. In some embodiments, the transparent icon may be back-lit.

The method may optionally include a step 610 of providing a second LC shutter residing co-axially with the graphic icon and the LC shutter. The second LC shutter, when driven, obscures the transparent icon portion of the LC shutter. In optional step 612, the control circuit may drive the second LC shutter off (transparent) and on (opaque), which causes the transparent icon to appear to flash on and off.

The described readiness indicator 62 has each of the properties that are desired in a more optimal display. The ready-for-use and not-ready-for-use states are easily recognizable. The use of familiar icons such as an X and a check-mark, in addition to the optional color scheme in the indicator meets is easily recognized by users from all countries as an indication that the device state is ready. In addition, the indicator is fail-safe. The not-ready-for-use state is displayed if power is not available to the device or if internal failure occurs in the device and the indicator is not actively driven to the "ready-for-use" state. The readiness indicator 62 is large enough to be seen across a room, while occupying only minimal space on the front panel of the medical device. Finally, the readiness indicator optionally provides a secondary and active indication that the medical device is ready for use by use of a second LC shutter mechanism which allows the transparent readiness icon 70 to flash, e.g. the invention can periodically black-out the white check mark to create an effect that the check mark is flashing.

Modifications to the device, method, and displays as described above are encompassed within the scope of the invention. For example, various configurations of the device controller and monitor circuits which fulfill the self-testing and display-driving objectives of the described invention fall within the scope of the claims. Also, the particular appearance and arrangement of the icons on the visual indicator may differ somewhat from that described.

It should be understood that, while the present invention has been described in terms of medical applications, the teachings of the present invention are much broader and are applicable for non-medical applications and uses. Further, As one having ordinary skill in the art will appreciate in view of the teachings provided herein, features, elements, components, etc. described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of systems, devices and methods in accordance with the present invention (which embodiments are intended to be illustrative and not limiting), it is noted that modifications and variations in/to such exemplary embodiments can be made by persons skilled in the art in light of the teachings provided herein (including the appended Figures). It is therefore to be understood that such changes which can be made in/to the preferred and exemplary embodiments of the present disclosure are within the scope of the present invention and the exemplary embodiments disclosed herein.

The invention claimed is:

1. A method for displaying the operating status of a defibrillator, comprising the steps of:
    automatically determining a ready-for-use status of the defibrillator in a defibrillator self-test circuit;
    providing a positive control signal from the defibrillator self-test circuit responsive to the automatically determining step;
    providing a second liquid crystal shutter coaxial with the visual icon and the liquid crystal shutter;
    providing a visual display on an external surface of the defibrillator, the visual display including a visual icon which indicates a not-ready-for-use status overlaid by a liquid crystal shutter; and
    driving the liquid crystal shutter to an opaque state with the positive control signal,
    wherein the liquid crystal shutter includes a transparent visual icon which indicates the ready-for-use status responsive to the driving step.

2. The method of claim 1, further comprising the step of:
    periodically cycling the second liquid crystal shutter to an opaque state with the positive control signal.

3. The method of claim 1, wherein the automatically determining step is conducted during at least one of a standby condition or during a clinical operating condition in the defibrillator.

4. A defibrillator having an external housing, comprising:
    a readiness status circuit operable to determine a ready-for-use status; and
    a visual indicator controlled by the readiness status circuit and disposed on the housing,
    the visual indicator including
    a graphic icon indicating a not-ready-for-use status, a liquid crystal shutter overlaying the graphic icon,
    the liquid crystal shutter having a transparent icon indicating a ready-for-use status,
    wherein the visual indicator further comprises: a second liquid crystal shutter disposed coaxially with both the liquid crystal shutter transparent icon and the graphic icon, and
    wherein the readiness status circuit is operable to drive a portion of the liquid crystal shutter surrounding the transparent icon into an opaque state.

5. The defibrillator of claim 4, wherein the graphic icon is disposed in the form of a white X surrounded by a colored background.

6. The defibrillator of claim 5, wherein the colored background is red.

7. The defibrillator of claim 4, wherein the transparent icon is disposed in the shape of a check mark.

8. The defibrillator of claim 7,
wherein the graphic icon is disposed in the form of a white X surrounded by a colored background, and
wherein the transparent icon overlays only the white X portion of the graphic icon.

9. The defibrillator of claim 4,
wherein the readiness status circuit is operable to periodically drive the second liquid crystal shutter to an opaque state.

10. The defibrillator of claim 4, wherein the liquid crystal shutter has a transparent state when de-energized, thereby exposing the graphic icon to view.

11. The defibrillator of claim 10, further comprising an audible output of a not-ready-for-use status controlled by the readiness status circuit.

12. A visual readiness indicator for a medical device, comprising:
an input for a signal indicating a ready-for-use status;
a graphic icon indicating a not-ready-for-use status; and
a liquid crystal shutter overlaying the graphic icon, the liquid crystal shutter having a transparent icon indicating a ready-for-use status,
a second liquid crystal shutter disposed coaxially with both the liquid crystal shutter transparent icon and the graphic icon,
wherein the input is operable to drive a portion of the liquid crystal shutter surrounding the transparent icon into an opaque state.

13. The visual readiness indicator of claim 12, wherein the graphic icon is disposed in the form of a white X surrounded by a colored background.

14. The visual readiness indicator of claim 13, wherein the colored background is red.

15. The visual readiness indicator of claim 12, wherein the transparent icon is disposed in the shape of a check mark.

16. The visual readiness indicator of claim 15,
wherein the graphic icon is disposed in the form of a white X surrounded by a colored background, and
wherein the transparent icon overlays only the white X portion of the graphic icon.

17. The visual readiness indicator of claim 12, further comprising:
wherein the readiness status circuit is operable to periodically drive the second liquid crystal shutter to an opaque state.

18. The visual readiness indicator of claim 12, wherein the liquid crystal shutter has a transparent state when de-energized, thereby exposing the graphic icon to view.

19. The visual readiness indicator of claim 18, further comprising an audible output of a not-ready-for-use status controlled by the readiness status circuit.

* * * * *